United States Patent [19]

Cross

[11] 4,003,732
[45] Jan. 18, 1977

[54] PYRAZOLINIUM COMPOUNDS AS HERBICIDES

[75] Inventor: Barrington Cross, Rocky Hill, N.J.

[73] Assignee: American Cyanamid Company, Stamford, Conn.

[22] Filed: July 28, 1975

[21] Appl. No.: 599,805

Related U.S. Application Data

[62] Division of Ser. No. 484,515, July 1, 1974, Pat. No. 3,925,408.

[52] U.S. Cl. .................................... 71/92; 71/86; 71/87; 71/90
[51] Int. Cl.$^2$ ........................................ A01N 9/22
[58] Field of Search ............ 71/92, 90; 260/310 R, 260/311

[56] References Cited

UNITED STATES PATENTS

| 3,882,142 | 5/1975 | Walworth et al. | 71/92 |
| 3,929,451 | 12/1975 | Cross et al. | 260/310 R |

OTHER PUBLICATIONS

Laboratoire Cetrane, "Antidiabetic 3–Pyrazolines," (1973), CA 80 No. 1209289, (1974).

*Primary Examiner*—Glennon H. Hollrah
*Attorney, Agent, or Firm*—Harry H. Kline

[57] ABSTRACT

This invention provides for 1,2-dialkyl-3,5-disubstituted and -3,4,5-trisubstituted pyrazolinium salts, a method for the preparation of the said compounds, and a method for controlling undesirable plant species therewith.

7 Claims, No Drawings

PYRAZOLINIUM COMPOUNDS AS HERBICIDES

This application is a divisional of my co-pending application, Ser. No. 484,515, filed on July 1, 1974, now U.S. Pat. No. 3,925,408, which issued on Dec. 9, 1975.

This invention relates to pyrazolinium salts represented by the formula:

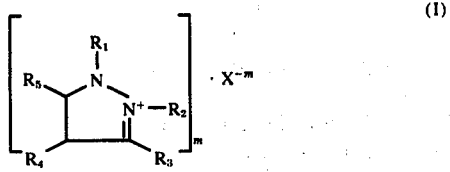

wherein $R_1$ and $R_2$ each represent alkyl $C_1$–$C_4$; $R_4$ represents a member selected from the group consisting of hydrogen, methyl, methoxy, methylthio, methylsulfinyl and methylsulfonyl; $R_3$ and $R_5$ each represent members selected from the group consisting of cycloalkyl $C_3$–$C_7$, cycloalkylmethyl $C_3$–$C_7$, methylcycloalkyl $C_3$–$C_7$, cycloalkenyl $C_3$–$C_7$, alkyl $C_2$–$C_{11}$, thienyl and

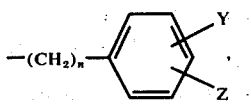

provided that when $R_4$ is hydrogen, at least one of $R_3$ and $R_5$ is a member other than phenyl; X represents an anion having a charge of from 1 to 3, and preferably 1 or 2; $n$ is an integer selected from 0 and 1; $m$ is an integer selected from 1, 2 and 3; and Y and Z each represent members selected from the group consisting of hydrogen, halogen, nitro, cyano, alkyl $C_1$–$C_4$, alkoxy $C_1$–$C_4$ and $CF_3$.

Illustrative of the anions which are suitable for use in the present invention may be mentioned, for example, halides, such as chloride, bromide or iodide; acetate; sulfate, hydroxide; hydrogen sulfate; methyl sulfate; benzene sulfonate; $C_1$–$C_4$ alkoxy benzene sulfonate; $C_1$–$C_3$ alkyl benzene sulfonate, preferably a toluene sulfonate, such as p-toluene sulfonate; nitrate; phosphate; carbonate; hydrogen carbonate; alkane sulfonate $C_1$–$C_4$; perchlorate;

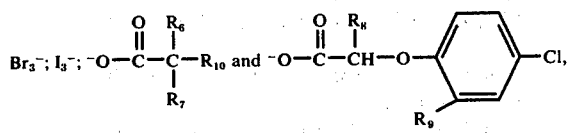

wherein $R_{10}$ is halogen, methyl, halomethyl or dihalomethyl; $R_6$ and $R_7$ are each halogen; $R_8$ is hydrogen or methyl; and $R_9$ is chlorine or methyl.

With regard to pyrazolinium salts of the present invention, it is to be understood that certain multivalent anions such as sulfate, phosphate, and the like, may have associated with them a cation in addition to the pyrazolium cation, as for example, a proton or an alkali metal or alkaline earth metal. For simplicity, such anions are portrayed as being unionized although they probably are in fact further ionized. Typical representations are: $NaSO_4^-$, $KPO_4^-$, $MgPO_4^-$, $HSO_4^-$, $NaHPO_4^-$, and the like.

Unless otherwise defined, the term "halogen," as used herein, is intended to mean chlorine, bromine, iodine and fluorine.

Preferred compounds of the invention have the above structure, wherein $R_1$ and $R_2$ are each methyl; $R_4$ is hydrogen, methyl, methylthio or methoxy; and $R_3$, $R_5$, X and m are as described above.

Still more preferred are compounds depicted by the above formula, wherein $R_1$ and $R_2$ are each methyl; $R_4$ is hydrogen, methyl or methoxy; $R_3$ and $R_5$ each represent a member selected from the group consisting of phenyl, monohalophenyl, monomethylphenyl, dimethylphenyl and cycloalkyl $C_3$–$C_7$, provided that when $R_4$ is hydrogen at least one of $R_3$ and $R_5$ is a member other than phenyl; X is an anion having a single charge; and $m$ is 1.

The invention, while relating to the compounds described by formula (I) above, also relates to a method for the preparation of said compounds and to a method for controlling undesirable plant species with said formula (I) compounds and derivatives thereof. The latter said derivatives are represented by the given formula, but also include compounds wherein $R_4$ is hydrogen, $R_3$ and $R_5$ are phenyl, and X and m are as defined above.

Advantageously, the pyrazolinium compounds of the invention can be prepared by several procedures. One procedure, hereinafter referred to as Procedure A, involves the condensation of an $\alpha,\beta$-unsaturated ketone with an equimolar amount, and preferably an excess of from 1 to 2 mole equivalents of a 1,2-dialkylhydrazine salt. This reaction is preferably conducted in the presence of a protonic solvent such as a lower alcohol $C_1$–$C_4$ or acetic acid, and usually requires elevated temperatures of from about 50° to 150° C, and preferably 75° to 100° C, and an extended reaction period of from about 2 hours to 2 weeks. A 24- to 48-hour reflux period is frequently employed; however, a shorter reflux period may be used. The pyrazolinium products can be isolated from unreacted chalcone by virtue of their water solubility. Isolation can be achieved by evaporation of the solvent from the reaction mixture, dissolution of the remaining residue in water, and extraction of impurities with ether. The appropriate salt of the pyrazolinium ion can then be obtained from the aqueous solution by evaporation of the water. The anion of the 1,2-dialkylhydrazine salt will be the anion of the pyrazolinium salt. Ion exchange chromatography may be used to exchange the anion of the pyrazolinium salt. The exchange may be affected by treating the initially formed salt with an ion exchange resin. Among the suitable ion exchange resins, one may mention a strong base organic anion exchanger, such a Dowex 1-x8. Illustrative exchangers employ quaternary ammonium salts. Where the resin is supplied as the salt of an anion other than that desired, it is pretreated with an aqueous solution of a salt of the desired anion. For example, if the resin is supplied as a quaternary ammonium chloride and it is desired to produce a pyrazolinium bromide, one would pretreat the resin with hydrobromic acid.

Other modifications of the anion in the pyrazolinium salt can also be affected. For example, a pyrazolinium chloride can be conveniently converted to the corresponding bromide or iodide by treatment with aqueous hydrogen bromide or aqueous sodium iodide, respectively.

In addition, the methyl sulfate can be exchanged for other anions such as $Cl^-$, $NO_3^-$ or $CH_3COO^-$ by adding to an aqueous solution of the methyl sulfate salt such salts as calcium chloride, calcium nitrate or calcium acetate either as a salt or as an aqueous solution. Insoluble calcium methyl sulfate precipitates and is removed by filtration. The desired pyrazolinium salt can be isolated as a solid from the aqueous medium by extraction with chloroform and then removal of the chloroform by evaporation.

The reaction of Procedure A may be graphically illustrated as follows:

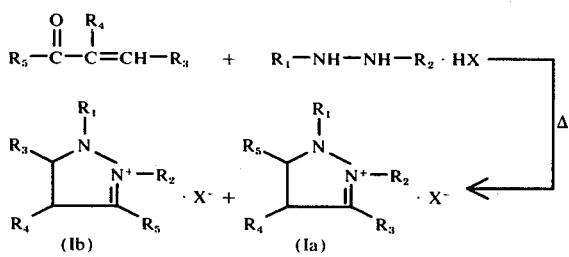

where $R_1$, $R_2$, $R_3$, $R_4$, $R_5$ and X are each as defined above. As shown, when $R_1=R_2$ Procedure A gives the predominant product as (Ib) involving reaction first at the carbonyl carbon center. Thus, this procedure can be used to prepare isomers (Ia) or (Ib) by selection of the appropriate starting chalcone.

Pyrazolinium compounds of the present invention depicted by formula (I) can also be prepared by reduction of the appropriate pyrazolium compound. This procedure is, hereinafter, referred to as Procedure B, and involves treatment of a pyrazolium salt with a reducing agent such as lithium aluminum hydride or sodium borohydride. the reduction with sodium borohydride is generally conducted in the presence of a solvent such as alcohol. Other suitable solvents include $C_1-C_6$ saturated alcohols, isopropyl alcohol being preferred. This reaction is generally carried out at an elevated temperature between about 20° and 100° C. using equimolar amounts of the pyrazolium compound and the reducing agent. The reduction with lithium aluminum hydride is conducted in other solvents such as diethyl ether, dimethyl ether, methylethyl ether, tetrahydrofuran, in the temperature range of from 20° to 100° C.

After the reduction, the resulting 3-pyrazoline is protonated with an appropriate acid, HX, to give the pyrazolinium salt. This reaction is graphically illustrated as follows using sodium borohydride as a representative reducing agent:

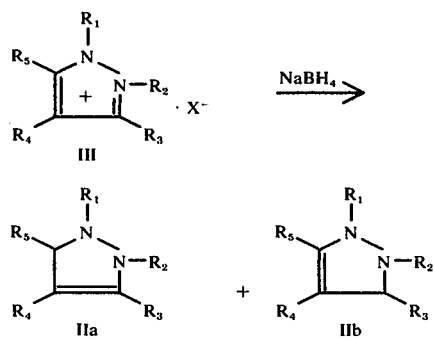

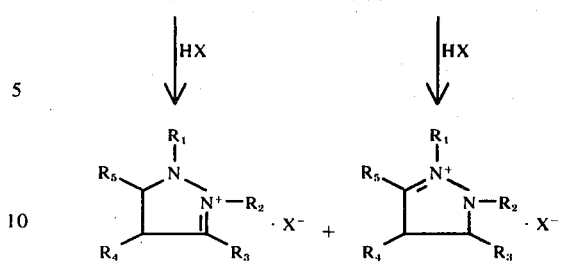

where $R_1$, $R_2$, $R_3$, $R_4$, $R_5$ and X are each as defined above.

The 3-pyrazolines (IIa and IIb) may be isolated directly from the reduction, if desired, by avoiding protonation in the work-up procedure.

Among the compounds which can be prepared by one or both of the above procedures are:

5-Benzyl-1,2-dimethyl-3-phenyl-2-pyrazolinium iodide;

3-Cyclohexyl-1,2-dimethyl-5-phenyl-2-pyrazolinium iodide;

3-Cyclohex-1-enyl-1,2-dimethyl-5-phenyl-2-pyrazolinium iodide;

5-Cyclohexyl-1,2-dimethyl-3-(p-fluorophenyl)-2-pyrazolinium methyl sulfate;

3,5-Dicyclohexyl-1,2,4-trimethyl-2-pyrazolinium perchlorate;

5-Cyclohexyl-1,2-dimethyl-3-pentyl-2-pyrazolinium chloride;

1,2-Dimethyl-3,5-di(2,4-xylyl)-2-pyrazolinium chloride;

3-Cyclohexyl-1,2-dimethyl-5-phenyl-2-pyrazolinium iodide;

3,5-Dicyclohexyl-1,2-dimethyl-2-pyrazolinium p-toluenesulfonate;

1,2-Dimethyl-3-(2-methylcyclohexyl)-5-phenyl-2-pyrazolinium iodide;

1,2-Dimethyl-3-(3-cyanophenyl)-5-phenyl-2-pyrazolinium iodide;

1,2,4-Trimethyl-3,5-diphenyl-2-pyrazolinium iodide;

5-(m-Fluorophenyl)-1,2-dimethyl-3-phenyl-2-pyrazolinium bromide;

5-(o-Fluorophenyl)-1,2-dimethyl-3-phenyl-2-pyrazolinium methyl sulfate;

5-(p-Fluorophenyl)-1,2-dimethyl-3-phenyl-2-pyrazolinium hydrogen sulfate;

3-(p-Fluorophenyl)-1,2-dimethyl-5-phenyl-2-pyrazolinium perchlorate;

1,2-Dimethyl-3-o-tolyl-5-p-tolyl-2-pyrazolinium iodide;

1,2-Dimethyl-5-o-tolyl-3-p-tolyl-2-pyrazolinium methyl sulfate;

1,2-Dimethyl-3,5-di-m-tolyl-2-pyrazolinium methyl sulfate;

3-(p-Chlorophenyl)-1,2-dimethyl-5-phenyl-2-pyrazolinium benzene sulfonate;

3-Cyclohexyl-1,2,4-trimethyl-5-phenyl-2-pyrazolinium perchlorate;

1,2-Dimethyl-3,5-di-o-tolyl-2-pyrazolinium iodide;

5-Anisyl-1,2-dimethyl-3-phenyl-2-pyrazolinium perchlorate;

1,2-Dimethyl-3-(p-nitrophenyl)-5-phenyl-2-pyrazolinium iodide;

1,2-Dimethyl-3-phenyl-5-thienyl-2-pyrazolinium iodide;

1,2-Dimethyl-3-phenyl-5-m-tolyl-2-pyrazolinium iodide; and 1,2-Dimethyl-5-phenyl-3-m-tolyl-2-pyrazolinium iodide.

The compounds of the present invention, as represented by formula (I) above, and derivatives thereof wherein $R_4$ is hydrogen and $R_3$ and $R_5$ are phenyl, are highly effective as herbicidal agents. They are particularly effective when used as postemergence herbicides and applied to the foliage of undesirable plants at a rate between about 0.5 pound and 10 pounds per acre, and preferably from 0.5 pound to 4 pounds per acre.

Surprisingly, we have found the compounds of this invention to be selective wild oat herbicides effective for the control of *Avena fatua*, *Avena ludoviciana* and *Avena sterilis* in the presence of crops such as barley, wheat and rice. They are also selective for controlling broadleaf weeds such as mustard, pigweed, velvetleaf and morningglory.

For application of the formula (I) pyrazolinium salts to the foliage of the undesirable plant species, the salts are generally formulated as postemergence herbicidal compositions by admixing a herbicidal adjuvant with a herbicidally effective amount of the salt. Suitable adjuvants include one or more conventional solid or liquid carriers, diluents and formulation aids, particularly surfactants.

The active compounds may be formulated as dusts, dust concentrates, wettable powders or water-miscible concentrates; however, the water-miscible concentrates are especially advantageous.

Dusts are readily prepared by grinding together about 1 to 25% by weight of the active agent with from about 99 to 75% by weight of a solid diluent such as kaolin, attapulgite, diatomaceous earth, or the like. Dust concentrates are prepared in similar fashion excepting that about 25 to 95% by weight of the active agent is ground with about 75 to 5% by weight of the diluent.

Wettable powders are prepared in the same manner as the dust concentrates excepting that about 1 to 5% by weight of a dispersing agent such as sodium lignosulfonate, or the sodium salt of condensed naphthalene sulfonic acid is blended with the mixture and about 1 to 5% of a surfactant, such as polyoxyethylated vegetable oil or an alkyl phenoxy polyoxyethylene ethanol, is also blended with the formulation. In practice, the powder is mixed with water and applied to the plant foliage as an aqueous spray.

Water-miscible concentrates are prepared by dissolving from 15 to 70% of the compound in 85 to 30% of a water-miscible solvent, such as water itself or another polar water-miscible solvent, such as 2-methoxy ethanol, methanol, propylene glycol, diethylene glycol, diethylene glycol monoethyl ether, formamide and methylformamide. Application of the material is made by adding a predetermined quantity of the water-miscible concentrate to a spray tank and applying the concentrate as such or in combination with an additional quantity of water or other polar solvent as a liquid spray.

The invention is further illustrated by the examples set forth below. These examples are provided only by way of illustration and are not intended to be limiting on the invention.

EXAMPLE 1

Preparation of 1,2-Dimethyl-3,5-diphenyl-2-pyrazolinium iodide.

Procedure A

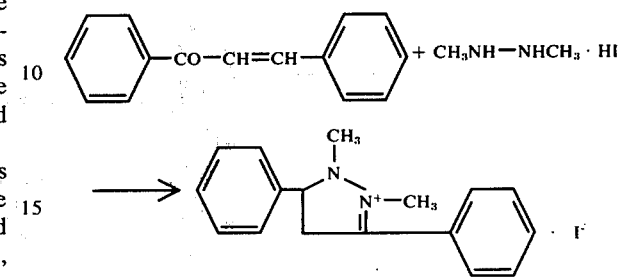

An absolute ethanol solution of sym-dimethylhydrazine dihydriodide [sym-dimethylhydrazine dihydriodide is prepared from sym-dimethylhydrazine dihydrochloride (13.3 g, 0.1 mole) in ethanol by refluxing with an excess of potassium iodide (33.2 g, 0.2 mole) for 3 hours], is added to an absolute ethanol suspension of chalcone (15.6 g). The reaction mixture is heated to reflux with constant stirring and maintained there for 18 hours. After allowing the reaction mixture to cool to room temperature, the solvent is removed by evaporation, and the resulting mixture stirred with an aqueous potassium iodide solution. The resulting solid is filtered and dried to give 5.95 g (21%), melting point 175° to 176° C of 1,2-dimethyl-3,5-diphenyl-2-pyrazolinium iodide.

EXAMPLE 2

Preparation of 1,2-Dimethyl-3,5-diphenyl-2-pyrazolinium perchlorate.

Procedure B

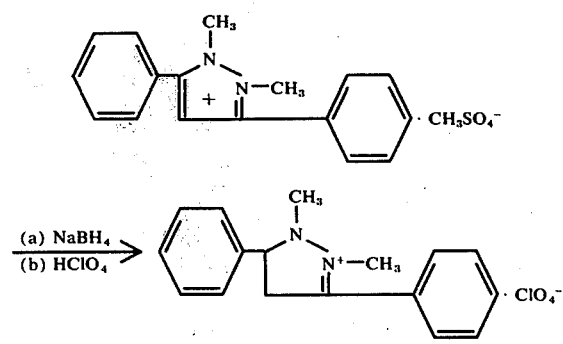

Sodium borohydride (1.95 g) is added to a partial solution of 1,2-dimethyl-3,5-diphenylpyrazolium methyl sulfate (17.75 g) in isopropanol (700 ml). The reaction mixture is heated to reflux with stirring and maintained at reflux for 6 hours. After allowing the reaction mixture to cool to room temperature, it is stirred for 12 hours. The solvent is then removed by evaporation, and the resulting mixture slurried in water and extracted with benzene. Evaporation of the organic layer yields an oil which is slurried in water and treated with perchloric acid. The aqueous solution is decanted away from the resulting tacky solid which is then treated with 95% ethanol. The resulting white solid is filtered and dried to yield 8.5 g (51%), melting point 183° to 185° C of 1,2-dimethyl-3,5-diphenyl-2-pyrazolinium perchlorate.

EXAMPLE 3

Following either Procedure A or Procedure B, as described in Examples 1 and 2 above, and employing (1) the appropriate α,β-unsaturated ketones and symmetrical dialkyl hydrazine salt, or (2) the appropriate 1,2-dialkyl-3,5-disubstituted pyrazolium salt, yields the compounds reported in Table I below.

TABLE I

Preparation of Pyrazolinium Salts having the Structure:

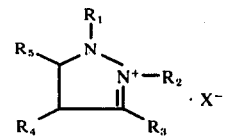

| $R_1$ | $R_2$ | $R_3$ | $R_4$ | $R_5$ | X | Method | Melting Point °C | Analysis Calculated | Found |
|---|---|---|---|---|---|---|---|---|---|
| $CH_3$ | $CH_3$ | phenyl | $CH_3$ | phenyl | I | A | 175–176 (dec.) | C, 55.10<br>H, 5.40<br>N, 7.14 | 55.22<br>5.45<br>7.15 |
| $CH_3$ | $CH_3$ | phenyl | H | 3-F-phenyl | I | A | 120–124 (dec.) | C, 51.52<br>H, 4.58<br>N, 7.07<br>I, 32.03 | 51.68<br>4.73<br>7.14<br>32.36 |
| $CH_3$ | $CH_3$ | phenyl | H | 2-F-phenyl | $ClO_4$ | A | 148–149 (dec.) | C, 55.50<br>H, 4.66<br>Cl, 9.64<br>F, 5.17<br>N, 7.62 | 56.06<br>4.74<br>9.78<br>5.10<br>7.59 |
| $CH_3$ | $CH_3$ | phenyl | H | 4-F-phenyl | I | A | 137–139 (dec.) | C, 51.52<br>H, 4.58<br>N, 7.07<br>I, 32.03 | 51.48<br>4.61<br>6.76<br>29.70<br>29.99 |
| $CH_3$ | $CH_3$ | 4-F-phenyl | H | phenyl | I | A | 165–167 | C, 51.52<br>H, 4.58<br>N, 7.07<br>I, 32.03 | 51.07<br>4.61<br>6.83<br>32.09 |
| $CH_3$ | $CH_3$ | phenyl | H | 4-CH₃-phenyl | I | A | 146–149 | C, 56.16<br>H, 5.71<br>N, 6.90 | 55.98<br>5.74<br>6.76 |
| $CH_3$ | $CH_3$ | 4-CH₃-phenyl | H | phenyl | I | A | 175–176 | C, 56.16<br>H, 5.71<br>N, 6.90 | 56.46<br>5.88<br>6.89 |
| $CH_3$ | $CH_3$ | phenyl | H | 3-CH₃-phenyl | I | A | 94–96 | C, 52.76<br>H, 5.58<br>N, 6.47<br>I, 31.24 | 53.01<br>5.38<br>6.38<br>29.44 |
| $CH_3$ | $CH_3$ | 4-Cl-phenyl | H | phenyl | $ClO_4$ | A | 161–166 | C, 53.00<br>H, 4.71<br>N, 7.28<br>Cl, 18.42 | 51.89<br>4.41<br>7.57<br>18.96 |
| $CH_3$ | $CH_3$ | 3-CH₃-phenyl | H | 3-CH₃-phenyl | I | A | 166–168 (dec.) | C, 56.16<br>H, 5.71<br>N, 6.90 | 55.88<br>5.59<br>6.76 |

TABLE I-continued

Preparation of Pyrazolinium Salts having the Structure:

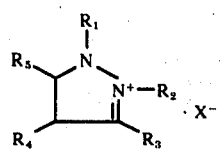

| $R_1$ | $R_2$ | $R_3$ | $R_4$ | $R_5$ | X | Method | Melting Point °C | Analysis Calculated | Found |
|---|---|---|---|---|---|---|---|---|---|
| $CH_3$ | $CH_3$ | 4-methoxyphenyl | H | phenyl | $ClO_4$ | A | 120–126 | C, 56.76<br>H, 5.56<br>N, 7.36<br>Cl, 9.31 | 56.52<br>5.62<br>7.22<br>9.35 |
| $CH_3$ | $CH_3$ | phenyl | H | 4-nitrophenyl | I | A | | | |
| $CH_3$ | $CH_3$ | phenyl | H | 2-thienyl | I | A | Low melting solid | | |
| $CH_3$ | $CH_3$ | phenyl | H | phenyl | $ClO_4^-$ | B | 184–185 | C, 58.21<br>H, 5.46<br>N, 7.99 | 58.15<br>5.29<br>7.84 |
| $CH_3$ | $CH_3$ | phenyl | H | phenyl | $I^-$ | A | 175–176 | C, 53.98<br>H, 5.07<br>N, 7.41 | 53.70<br>5.13<br>7.42 |
| $CH_3$ | $CH_3$ | phenyl | H | 3-methylphenyl | $I^-$ | A | 148–150 | C, 55.11<br>H, 5.40<br>N, 7.14 | 54.79<br>5.52<br>7.00 |
| $CH_3$ | $CH_3$ | 4-methylphenyl | H | 2-methylphenyl | $I^-$ | A | 143–145 | C, 55.11<br>H, 5.40<br>N, 7.14 | 54.80<br>5.48<br>7.05 |

EXAMPLE 4

The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% Tween 20, a polyoxyethylene sorbitan monolaurate surfactant by Atlas Chemical Industries, in sufficient quantity to provide the equivalent of about 10 pounds per acre of active compound when applied to the plants through a spray nozzle operating at 40 psi for a predetermined time. After spraying, the plants are placed on greenhouse benches and are cared for in the usual manner, commensurate with conventional greenhouse practices. Two weeks after treatment, the seedling plants are examined and rated according to the rating system provided below. The data obtained are reported in Table II below, where it can be seen that the compounds are highly effective for the control of lambsquarters, mustard and pigweed; specific compounds are also highly effective against ragweed, morningglory and velvetleaf.

| Rating System: | % Difference in Growth from the Check* |
|---|---|
| 0 - No effect | 0 |
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth, that is, a definite physiological malformation but with an over-all | |

-continued

GRF - Green foxtail (*Setaria viridis*)
WO - Wild oats (*Avena fatua*)
VL - Velvetleaf (*Abutilon theopharas*)

TABLE II

Postemergence Herbicidal Activity

| Structure | Treatment lb/Acre | LA | MU | PI | RAG | MG | BA | CR | GRF | WO | VL |
|---|---|---|---|---|---|---|---|---|---|---|---|
| 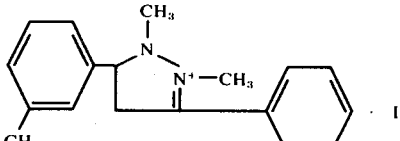 | 10 | 9 | 9 | 5 | 9 | 2 | 0 | 2 | 3 | *8 | 2 |
| 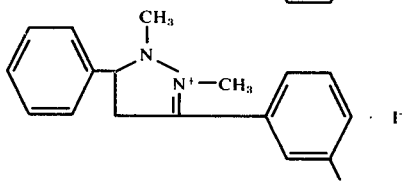 | 10 | 9 | 9 | 5 | 5 | 2 | 2 | 2 | 3 | *8 | 2 |
| 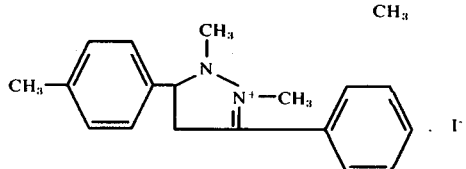 | 10 | 9 | 9 | 9 | 0 | 6 | 3 | 0 | 0 | *8 | 6 |
| 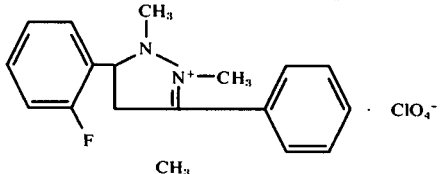 | 10 | 9 | 9 | 9 | 0 | 3 | 0 | 2 | 0 | *8 | 6 |
| 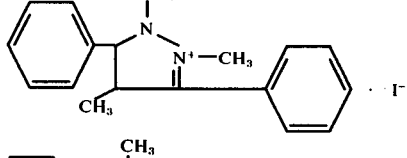 | 10 | 9 | 9 | 9 | 2 | 9 | 8 | 3 | 6 | 7 | 9 |
| 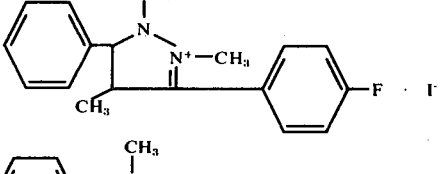 | 10 | 9 | 9 | 9 | 7 | 3 | 2 | 3 | 3 | *8 | 9 |
| 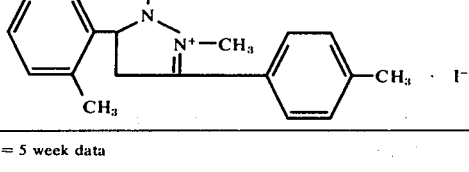 | 10 | 9 | 7 | 7 | 9 | 1 | 1 | 1 | 1 | *8 | 6 |

* = 5 week data

Rating System: from the Check*
effect less than a 5 on the rating scale.

*Based on visual determination of stand, size, vigor, chlorosis, growth malformation and over-all plant appearance.

Plant Abbreviations
LA - Lambsquarters (*Chenopodium album*)
MU - Mustard (*Brassica kaber*)
PI - Pigweed (*Amaranthus retroflexus*)
RAG - Ragweed (*Ambrosia artemisiifolia*)
MG - Morningglory (*Ipomoca purpurea*)
BA - Barnyardgrass (*Echinochloa crusgalli*)
CR - Crabgrass (*Digitaria sanguinalis*)

EXAMPLE 5

The pronounced selective postemergence herbicidal activity of the compounds of this invention is demonstrated in the following tests. The test procedure employed is essentially the same as that described for the postemergence tests, described in the preceding example; however, the compounds are applied at rates of from 0.5 pound to 9 pounds per acre, and crop plants such as barley, wheat and rice are used to determine selectivity. Wild oat data are taken at 5 weeks along with crop readings.

Data obtained are reported in Table III below, where it can be seen that the compounds of the present invention are highly effective for controlling mustard, pigweed, velvetleaf, wild oats and morningglory, but cause little or no injury to barley (*Hordeum vulgare*); and with selected compounds, little or no injury to wheat (*Triticum vulgare*) and/or rice (*Oryza sativa*).

Additional Plant Abbreviations
BR - Barley (*Hordeum vulgare*)
MU - Wild Mustard (*Brassica kaber*)
WH - Wheat (*Triticum vulgare*)
RI - Rice (*Oryza sativa*)

TABLE III

Selective Postemergence Herbicidal Activity

| Structure | Treatment lb/Acre | BR | MU | WH | PI | BA | CR | GRF | WO | MG | RI | VL |
|---|---|---|---|---|---|---|---|---|---|---|---|---|
| 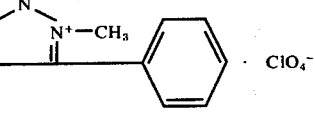 | 4 | 0 | 9 | 1 | 9 | 0 | 2 | 1 | 8 | 1 | 3 | 9 |
|  | 1 | 0 | 9 | 1 | 9 | 0 | 2 | 1 | 8 | 1 | 2 | 3 |
|  | 0.5 | 0 | 7 | 0 | 3 | 0 | 2 | 1 | 8 | 1 | 2 | 3 |
| 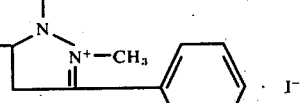 | 4 | 0 | 8 | 3 | 9 | 2 | 9 | 9 | 8 | 5 | 0 | 5 |
|  | 1 | 0 | 5 | 0 | 1 | 0 | 5 | 1 | 7 | 1 | 0 | 5 |
|  | 0.5 | 0 | 5 | 0 | 0 | 0 | 3 | 0 | 3 | 1 | 0 | 5 |
| 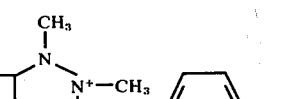 | 4 | 0 | 9 | 6 | 9 | 1 | 1 | 0 | 3 | 1 | 6 | 9 |
|  | 1 | 0 | 9 | 5 | 5 | 0 | 0 | 0 | 8 | 0 | 3 | 2 |
|  | 0.5 | 0 | 5 | 5 | 0 | 0 | 0 | 0 | 9 | 0 | 2 | 3 |
|  | 4 | 0 | 9 | 6 | 9 | 1 | 0 | 1 | 7 | 9 | 2 | 9 |
|  | 1 | 0 | 7 | 5 | 2 | 0 | 0 | 0 | 8 | 2 | 1 | 7 |
|  | 0.5 | 0 | 3 | 5 | 0 | 0 | 0 | 0 | 9 | 0 | 1 | 2 |
| 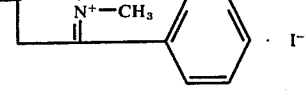 | 4 | 0 | 9 | 5 | 9 | 0 | 7 | 1 | 6 | 9 | — | 8 |
|  | 1 | 0 | 7 | 3 | 9 | 0 | 2 | 1 | 2 | 6 | — | 6 |
|  | 0.5 | 0 | 3 | 2 | 8 | 0 | 0 | 1 | 8 | 3 | — | 3 |
| 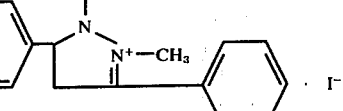 | 4 | 0 | 9 | 2 | 9 | 0 | 5 | 3 | 8 | 6 | — | 5 |
|  | 1 | 0 | 5 | 0 | 1 | 0 | 0 | 0 | 8 | 6 | — | 3 |
|  | 0.5 | 0 | 2 | 0 | 1 | 0 | 0 | 0 | 8 | 5 | — | 1 |
|  | 4 | 0 | 9 | 1 | 9 | 2 | 3 | 2 | 7 | 7 | — | 8 |
|  | 1 | 0 | 3 | 0 | 8 | 1 | 1 | 1 | 8 | 5 | — | 5 |
|  | 0.5 | 0 | 2 | 0 | 3 | 1 | 0 | 1 | 3 | 2 | — | 3 |
| 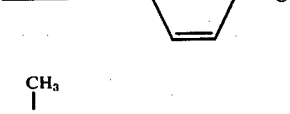 | 4 | 1 | 8 | 6 | 9 | 0 | 3 | 6 | 7 | 2 | — | 6 |
|  | 1 | 0 | 2 | 6 | 3 | 0 | 2 | 2 | 8 | 2 | — | 3 |
|  | 0.5 | 0 | 0 | 3 | 3 | 0 | 2 | 2 | 7 | 1 | — | 1 |

TABLE III-continued

Selective Postemergence Herbicidal Activity

| Structure | Treatment lb/Acre | BR | MU | WH | PI | BA | CR | GRF | WO | MG | RI | VL |
|---|---|---|---|---|---|---|---|---|---|---|---|---|
| (Ph)(CH₃)N-N⁺(CH₃)=CH-Ph · I⁻ | 4 | — | 8 | 3 | 9 | 2 | 9 | 9 | 8 | 5 | 0 | 9 |
| | 1 | — | 5 | 0 | 1 | 0 | 5 | 1 | 7 | 1 | 0 | 3 |
| | 0.5 | — | 5 | 0 | 0 | 0 | 3 | 0 | 5 | 1 | 0 | 3 |
| 3-F-Ph derivative · I⁻ | 9 | — | 9 | — | 9 | 6 | 8 | 7 | 7 | 7 | 9 | 9 |
| | 3 | — | 8 | — | 9 | 1 | 3 | 2 | 5 | 2 | 2 | 2 |
| | 1 | — | 3 | — | 3 | 0 | 1 | 1 | 3 | 1 | 1 | 0 |
| 2-CH₃-Ph, 2-CH₃-Ph derivative · I⁻ | 9 | — | 9 | — | 8 | 2 | 1 | 5 | 2 | 3 | 2 | 8 |
| | 3 | — | 7 | — | 7 | 0 | 1 | 3 | 1 | 3 | 0 | 2 |
| | 1 | — | 3 | — | 5 | 1 | 1 | 2 | 1 | 1 | 0 | 0 |
| 4-F-Ph derivative · I⁻ | 9 | — | 9 | — | 8 | 2 | 2 | 3 | 5 | 6 | 1 | 9 |
| | 3 | — | 7 | — | 7 | 1 | 1 | 2 | 5 | 3 | 0 | 7 |
| | 1 | — | 3 | — | 3 | 0 | 0 | 0 | 3 | 1 | 0 | 2 |
| 3-OCH₃-Ph derivative · ClO₄⁻ | 9 | — | 9 | — | 7 | 2 | 2 | 2 | 5 | 2 | 2 | 2 |
| | 3 | — | 7 | — | 3 | 1 | 1 | 1 | 2 | 2 | 2 | 1 |
| | 1 | — | 7 | — | 3 | 0 | 0 | 1 | 1 | 1 | 2 | 0 |
| 3-CH₃-Ph, 3-CH₃-Ph derivative · I⁻ ½H₂O | 4 | — | 9 | — | 9 | 2 | 3 | 5 | 7 | 9 | 5 | 9 |
| | 1 | — | 9 | — | 9 | 3 | 2 | 3 | 7 | 9 | 3 | 9 |
| | 0.5 | — | 8 | — | 8 | 1 | 1 | 2 | 4 | 6 | 3 | 7 |
| 4-Cl-Ph derivative · ClO₄⁻ | 9 | — | 9 | — | 7 | 3 | 2 | 2 | 7 | 3 | 4 | 5 |
| | 3 | — | 8 | — | 8 | 3 | 1 | 1 | 7 | 1 | 2 | 6 |
| | 1 | — | 5 | — | 8 | 1 | 1 | 1 | 4 | 1 | 2 | 3 |

I claim:
1. A method for the control of undesirable plant species comprising, contacting said undesirable plant species with a herbicidally effective amount of a compound having the formula:

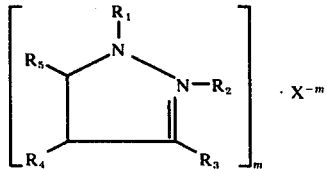

wherein $R_1$ and $R_2$ each represent alkyl $C_1-C_4$; $R_4$ represents a member selected from the group consisting of hydrogen, methyl, methoxy, methylthio, methylsulfinyl and methylsulfonyl; $R_3$ and $R_5$ each represent members selected from the group consisting of cycloalkyl $C_3$–$C_7$, cycloalkylmethyl $C_3$–$C_7$, methylcycloalkyl $C_3$–$C_7$, cycloalkenyl $C_3$–$C_7$, alkyl $C_2$–$C_{11}$, thienyl and

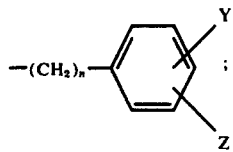

X represents an anion having a charge of from 1 to 3; $n$ is an integer selected from 0 and 1; $m$ is an integer selected from 1, 2 and 3; and Y and Z each represent members selected from the group consisting of hydrogen, halogen, nitro, cyano, alkyl $C_1$–$C_4$, alkoxy $C_1$–$C_4$ and $CF_3$.

2. A method according to claim 1, wherein the compound applied has the formula of said claim 1, wherein $R_1$ and $R_2$ are each methyl; $R_4$ is a member selected from the group consisting of hydrogen, methyl, methylthio and methoxy; and $R_3$, $R_5$, X and $m$ are as defined in said claim 1.

3. A method according to claim 1, wherein said compound is applied to the foliage of undesirable plants in an amount sufficient to provide from 0.5 pound to 10 pounds per acre of said active compound.

4. A method according to claim 1, wherein the compound applied has the formula of said claim 1, wherein $R_1$ and $R_2$ are each methyl; $R_4$ represents a member selected from the group consisting of hydrogen, methyl and methoxy; $R_3$ and $R_5$ each represent a member selected from the group consisting of phenyl, monohalophenyl, mono-methylphenyl, dimethylphenyl and cycloalkyl $C_3$–$C_7$; X is an anion having a single charge; and $m$ is 1.

5. A method for the selective postemergence control of undesirable plant species in the presence of crops selected from the group consisting of barley, wheat and rice, comprising: applying to the foliage of said undesirable plant species about 0.5 pound to 4 pounds per acre of a compound according to claim 1.

6. A method according to claim 5, wherein the undesirable plant species is wild oat.

7. A method according to claim 5, wherein the compound is a 3,5-diphenyl-1,2-dimethyl-2-pyrazolinium salt and the undesirable plant species is wild oat.

* * * * *